United States Patent
Wang et al.

(10) Patent No.: US 11,490,577 B2
(45) Date of Patent: Nov. 8, 2022

(54) IN VITRO RESCUE METHOD FOR IMMATURE EMBRYO OF AVOCADO

(71) Applicants: HAIKOU EXPERIMENTAL STATION, CHINESE ACADEMY OF TROPICAL AGRICULTRAL SCIENCES, Haikou (CN); SANYA RESEARCH INSTITUTE OF CHINESE ACADEMY OF TROPICAL AGRICULTURAL SCIENCES, Sanya (CN)

(72) Inventors: Jiashui Wang, Haikou (CN); Yanxia Li, Haikou (CN); Yuanzheng Liu, Haikou (CN); Weihong Ma, Haikou (CN); Xiaoping Zang, Haikou (CN); He Zhang, Haikou (CN)

(73) Assignees: HAIKOU EXPERIMENTAL STATION, CHINESE ACADEMY OF TROPICAL AGRICULTRAL SCIENCES, Haikou (CN); SANAY RESEARCH INSTITUTE OF CHINESE ACADEMY OF TROPICAL AGRICULTURAL SCIENCES, Sanya (CN)

( * ) Notice: Subject to any disclaimer, the term of this patent is extended or adjusted under 35 U.S.C. 154(b) by 0 days.

(21) Appl. No.: 17/594,036

(22) PCT Filed: Mar. 30, 2021

(86) PCT No.: PCT/CN2021/084039
§ 371 (c)(1),
(2) Date: Sep. 30, 2021

(87) PCT Pub. No.: WO2021/213152
PCT Pub. Date: Oct. 28, 2021

(65) Prior Publication Data
US 2022/0142076 A1   May 12, 2022

(30) Foreign Application Priority Data
Apr. 21, 2020   (CN) .......................... 202010319164.6

(51) Int. Cl.
*A01H 5/00*   (2018.01)
*A01H 4/00*   (2006.01)

(52) U.S. Cl.
CPC ............. *A01H 4/005* (2013.01); *A01H 4/002* (2021.01)

(58) Field of Classification Search
CPC .................. A01H 4/005; A01H 4/002
See application file for complete search history.

(56) References Cited

FOREIGN PATENT DOCUMENTS

| CN | 106688376 A | 5/2017 |
|---|---|---|
| CN | 108308030 A | 7/2018 |
| CN | 111543319 A | 8/2020 |
| ES | 2134133 B1 | 9/1999 |

OTHER PUBLICATIONS

Carimi et al. In vitro rescue of zygotic embryos of sour orange, *Citrus aurantium* L., and their detection based on RFLP analysis, Plant Breeding 117, 261-266 (1998). (Year: 1998).*
Daniel et al. Effect of L-gultamine and casein hydrolysale in the development of somatic embryos from cotyledonary leaf explants in okra (*Abelmoschus esculentus* L. *monech*), South African Journal of Botany 114 (2018) 223-231. (Year: 2018).*
Dodds et al. Experiments in Plant Tissue Culture, 2nd edition (1988) pp. 35-36 and 210-211. (Year: 1988).*
Hiti-Bandaralage et al. Micropropagation of Avocado (persea americana Mill.) American Journal of Plant Sciences, 2017, 8, 2898-2921. (Year: 2017).*
Klimaszewska et al. Influence of gelling agents on culture medium gel strength, water availability, tissue water potential, and maturation response in embryogenic cultures of *Pinus strobus* L., In Vitro Cell. Dev. Biol.-Plant 36:279-286, 2000. (Year: 2000).*
Marquez-Martin et al. Effects of an in vitro maturation treatment on plant recovery from avocado zygotic embryos, Scientia Horticulturae 122 (2009) 532-539. (Year: 2009).*
Rohim et al. In vitro rescue and regeneration of zygotic embryos of Avocado (Persea americana Mill.) cv. Hass, Journal of Applied Sciences Research, 9(7): 4132-4141,2013. (Year: 2013).*
Sanchez-Romero et al. In vitro rescue of immature avocado (Persea americana Mill.) embryos, Scientia Horticulturae 111 (2007) 365-370. (Year: 2007).*
Zhang et al. Embryo development in association with asymbiotic seed germination in vitro of Paphiopedilum armeniacum S. C. Chen et F. Y. Liu, Scientific Reports 5:16356, 1-15, 2015. (Year: 2015).*
Gao Qinghua. Advances in Research on Embryo Rescue Breeding of Fruit. Biotechnology Bulletin. Jul. 26, 2008 (Jun. 26, 2008). Supplementary issue, 6 pp. total.

* cited by examiner

Primary Examiner — June Hwu

(57) ABSTRACT

An in vitro rescue method for immature embryo of avocado includes: collecting immature avocado hybrid fruits, stripping immature zygotic embryos from the sterilized fruits; inducing maturation of zygotic embryos in different media selected according to the maturities of zygotic embryos; and avocado seed embryos growing to normal plants under light conditions after germination. Provided is a technology for the in vitro culture rescue of immature embryo of avocado, wherein the zygotic embryos at different developmental stages are induced to maturation under in vitro conditions, and after maturation, the seed embryos are induced to germinate and form healthy plants. The present invention can effectively improve the survival rate of hybrid avocado zygotic embryo, increase the success rate of hybrid avocado, rescue the hybrid offspring, reduce the loss of hybrid offspring, ensure the genetic integrity of hybrid group, and provide the key technology for hybrid breeding and genetic research of avocado.

8 Claims, 2 Drawing Sheets

IN VITRO RESCUE METHOD FOR IMMATURE EMBRYO OF AVOCADO

FIELD OF THE INVENTION

The present invention relates to an economic fruit tree breeding field, and specifically to an in vitro rescue method for immature embryo of avocado.

BACKGROUND OF THE INVENTION

Cross breeding of avocado is the main technology to create genetic variation, improve genetic characteristics and cultivate new varieties of fine plants. Through the interspecific cross of avocado, two or more excellent traits within the same species can be concentrated in a new variety. In addition, interspecific cross can also produce hybrid vigor, and obtain new varieties that are stronger or perform better than parental varieties.

However, young fruits of avocado have a high rate of falling. Using hybridization method for hybridizing, a large number of hybrid fruit will drop, and few of them can develop normally on trees, which leads to a huge loss of hybrid culture materials of avocado, which is also a major problem in avocado hybrid breeding. In the present invention, studies on this difficult problem are made, and a method to rescue and mature the zygotic embryos of fallen hybrid avocado fruits is put forward, which can effectively improve the survival rate of zygotic embryos of hybrid avocado, increase the success rate of avocado hybridization, save hybrid offspring, reduce the loss of hybrid offspring, ensure the genetic integrity of hybrid population, and provide key technologies for hybrid breeding and genetic research of avocado.

BRIEF SUMMARY OF THE INVENTION

Aiming at the problems in the prior art, provided is a method for culturing mature avocado seed embryos from peeled avocado fruits by using immature embryos for in vitro culture in the present invention. The rescued avocado seeds are able to germinate and grow into normal hybrid avocado plants.

In the present invention, "seed embryo", "zygotic embryo" and "embryo body" all refer to the core objects rescued by the method of the present invention, and these terms are interchangeable in the context of the present invention. In different specific contexts, different terms are used.

Media used in the method of the present invention for rescuing immature avocado seed embryos include:
(I) Basal Medium
(a) Basal medium is the basic nutrient solution for seed embryo germination, consisting of macroelements, trace elements, iron salts, and organic components;
(II) Germination Medium
germination medium is the nutrient solution for seed embryo germination and consists of basal medium+6-benzylaminopurine (6-BA)+agar powder+sucrose;
(III) Accompanying Medium
for the seed embryos of avocado with maturity less than 80%, the growth of seed embryos need to be promoted artificially by using accompanying medium because of low maturity; the accompanying medium consists of full-strength or half-strength basal medium+casein hydrolysate or glutamate+agar powder+sucrose.

As shown in the FIG. 1, the method of the present invention comprises the following steps:
Step S1, Pre-Treatment of Explants
collecting the fallen fruits of the immature avocado, stripping the immature zygotic embryos from the sterilized fallen fruits; selecting the zygotic embryos with maturity below 80%, accompanying culture to 80-100% maturity, and then germination culture.
collecting immature fallen fruits of avocado, stripping the immature zygotic embryos from the sterilized fallen fruits; increasing the maturity of the zygotic embryos with maturity below 80%, and then performing a germination culture
Step S2, Preparing the Basal Medium, the Accompanying Media and the Germination Medium According to the Dispensation,
wherein the dispensation of basal medium is shown in table 1 below:

TABLE 1

| | Ingredients of basal medium (mg/L) | working concentration of basal medium (mg/L) |
|---|---|---|
| Macroelements: | Potassium nitrate $KNO_3$ | 1600-2200 |
| | Ammonium nitrate $NH_4NO_3$ | 1500-1800 |
| | Potassium dihydrogen phosphate $KH_2PO_4$ | 150-180 |
| | Magnesium sulfate $MgSO_4 \cdot 7H_2O$ | 350-400 |
| | Calcium chloride $CaCl_2 \cdot 2H_2O$ | 420-460 |
| Trace elements: | Potassium iodide KI | 0.60-0.9 |
| | Boric acid $H_3BO_3$ | 2.0-4.0 |
| | Manganese sulfate $MnSO_4 \cdot 4H_2O$ | 8-12 |
| | Zinc sulfate $ZnSO_4 \cdot 7H_2O$ | 1.5-2.5 |
| | Sodium molybdate $Na_2MoO_4 \cdot 2H_2O$ | 0.20-0.30 |
| | Cobalt chloride $CoCl_2 \cdot 6H_2O$ | 0.020-0.30 |
| | Cupric sulfate $CuSO_4 \cdot 5H_2O$ | 0.020-0.30 |
| Iron salt: | Ethylenediaminetetraacetic acid disodium salt $Na_2 \cdot EDTA$ | 35-40 |
| | Ferrous sulfate $FeSO_4 \cdot 7H_2O$ | 25-30 |
| Organic composition: | Inositol | 80-120 |
| | Nicotinic acid VB5 | 0.8-1.2 |
| | Pyridoxine hydrochloride VB6 | 0.8-1.2 |
| | Thiamine hydrochloride VB1 | 0.8-1.2 | the dispensations of accompanying media a, b, c, d, e and f are as follows
a. Half-Strength Basal Medium
300 to 500 mg/L casein hydrolysate
8-12% coconut water
8 to 12% sucrose
1 to 3 g/L agar powder;
b. Half-Strength Basal Medium
300–500 mg/L glutamine
8-12% coconut water
8 to 12% sucrose
1-3 g/L agar powder
c. Half-Strength Basal Medium
300-500 mg/L casein hydrolysate
8-12% coconut water
4-6% sucrose
2-4 g/L agar powder;
d. Half-Strength Basal Medium
300-500 mg/L glutamine
8-12% coconut water
4-6% sucrose
2-4 g/L agar powder
e. Basal Medium
300-500 mg/L casein hydrolysate
8-12% coconut water
2-4% sucrose
4-6 g/L agar powder;
f. Basal Medium
300-500 mg/L glutamine
8-12% coconut water
4-6% sucrose
4-6 g/L agar powder,
adding each component other than coconut water to the vessels respectively, stirring, and then adjusting a pH of each medium to 5.5-6.5, after sterilizing and cooling the media, adding filtered and sterilized coconut water to the cooled sterilized medium to obtain the accompanying media a, b, c, d, e, and f.

The germination medium is formulated as
Basal Medium
2.0-4.0 μM 6-benzylaminopurine (6-BA)
4-8 g/L agar powder
2.5-3.5% sucrose;
Step S3, Selection of Initial Accompanying Media
selection of the appropriate dispensation of the accompanying media according to the different maturities of the zygotic embryos;
for seed embryos within 100 days after pollination, selecting either of the accompanying medium a or b as the initial accompanying medium;
for seed embryos between 100 and 200 days after pollination, selecting either of accompanying medium c or d as the initial accompanying medium;
for seed embryos after 200 days after pollination, either of accompanying medium e or f is selected as the initial accompanying medium;
Step S4, Accompanying Culture of Zygotic Embryos and the Selection and Replacement of Accompanying Medium In the pre-heart-shape stage of zygotic embryos, the accompanying medium a or b is used for accompanying culture (the accompanying culture in this stage is also known as "preliminary accompanying culture"); when the zygotic embryos are cultured into the torpedo stage, the accompanying medium is replaced by the accompanying medium c or d for accompanying culture (the accompanying culture in this stage is also known as "level one accompanying culture"). When the zygotic embryos are cultured into the maturation stage, the accompanying medium is replaced by the accompanying medium e or f for accompanying culture (the accompanying culture of this time is also known as "accompanying culture").

The time of zygotic embryo culture to maturity is set within 10 weeks; in these 10 weeks, no matter in which degree of maturity, the zygotic embryos could basically be cultured to maturity through accompanying culture within 10 weeks. With the increase of zygotic embryo maturity, the accompanying media are required to be replaced constantly. Generally, the zygotic embryos with a certain degree of maturity are cultured with the corresponding accompanying medium, and with the increase of maturity, the accompanying medium is replaced by the accompanying medium for higher maturity every 3-4 weeks. For example, in the pre-heart-shape stage, the accompanying medium a is used for the accompanying culture; after 3-4 weeks, the zygotic embryos develop into the torpedo stage, and now, the accompanying medium is replaced by accompanying medium c for further accompanying culture.

After the accompanying culture, the zygotic embryos have developed into the maturation stage, followed by the germination culture.

The accompanying culture of immature zygotic embryos is carried out under dark conditions.

Step S5, Germination Culture

The seed embryos obtained from the above accompanying culture were put into the germination medium and the germination culture is carried out at 25° C. 1° C. to maintain the growth of zygotic embryos; light culture is carried out during the germination culture until they were cultured into normal rooted seedlings. During germination, cotyledons on the accompanying medium are partially removed to induce the germination of the embryos; the germination is performed during 15 weeks and the germination medium is replaced approximately every 3 weeks.

The method according to the present invention, in step S1, the surface of fallen fruits and the seeds are sterilized.

According to the method of the present invention, the sterilization treatment comprises: soaking in a 0.5 v/v % sodium hypochlorite solution followed by rinsing in sterile distilled water for three times; preferably, the said 0.5 v/v % sodium hypochlorite solution further contains 10 drops/L of TWEEN 20.

According to the method of the present invention, in step S2, the dispensation of said germination medium is:
basal medium:
2.22 μM 6-BA;
6 g/L agar powder,
2.5-3.5% sucrose;
wherein the dispensation of said basal medium is formulated as shown in table 2 below:

TABLE 2

| | Ingredients of basal medium (mg/L) | working concentration (mg/L) |
|---|---|---|
| Macroelements: | Potassium nitrate KNO$_3$ | 1900 |
| | Ammonium nitrate NH$_4$NO$_3$ | 1650 |
| | Potassium dihydrogen phosphate KH$_2$PO$_4$ | 170 |
| | Magnesium sulfate MgSO$_4$•7H$_2$O | 370 |
| | Calcium chloride CaCl$_2$•2H$_2$O | 440 |
| Trace elements: | Potassium iodide KI | 0.75 |
| | Boric acid H$_3$BO$_3$ | 3.0 |
| | Manganese sulfate MnSO$_4$•4H$_2$O | 10 |
| | Zinc sulfate ZnSO$_4$•7H$_2$O | 2.0 |
| | Sodium molybdate Na$_2$MoO$_4$•2H$_2$O | 0.25 |
| | Cobalt chloride CoCl$_2$•6H$_2$O | 0.025 |
| | Cupric sulfate CuSO$_4$•5H$_2$O | 0.025 |
| Iron salt: | Ethylenediaminetetraacetic acid disodium salt Na$_2$•EDTA | 37.3 |
| | Ferrous sulfate FeSO$_4$•7H$_2$O | 27.8 |
| Organic composition: | Inositol | 100 |
| | Nicotinic acid VB5 | 1.0 |
| | Pyridoxine hydrochloride VB6 | 1.0 |
| | Thiamine hydrochloride VB1 | 10. |

In the method according to the present invention, in step S2, the dispensations of the accompanying media a, b, c, d, e and f are as follows.
a. Half-Strength Basal Medium
400 mg/L casein hydrolysate
10% coconut water
10% sucrose
2 g/L agar powder,
b. Half-Strength Basal Medium
400 mg/L glutamine
10% coconut water
10% sucrose
2 g/L agar powder
c. Half-Strength Basal Medium
400 mg/L casein hydrolysate
10% coconut water
5% sucrose
3 g/L agar powder,
d. Half-Strength Basal Medium
400 mg/L glutamine
10% coconut water
5% sucrose
3 g/L agar powder
e. Basal Medium
400 mg/L casein hydrolysate
10% coconut water
3% sucrose
5 g/L agar powder,
f. Basal Medium
400 mg/L glutamine
10% coconut water
3% sucrose
5 g/L agar powder.

In the step S3, according to the method of the present invention, for the seed embryos within 100 days after pollination, if the initial accompanying culture is selected for poor results or poor development, the seeds are maintained at a temperature of 25° C. 1° C. using a pre-culture medium after stripping them of their seed coats and sterilizing them, with 16 hours of light irradiation during the maintenance of growth (as shown in FIG. 2), and when the seeds return to normal growth, according to the above steps continuing the rescue of immature embryos;
for the seed embryos within 100 days after pollination with a poor effect of the initial accompanying culture selected or a poor development, after stripping the seeds of their seed coats and sterilizing them, keeping the seeds growing at a temperature of 25° C. 1° C. in a pre-culture medium, with 16 hours of light irradiation during the growth, and continuing the rescue of immature embryos after the seeds return to normal growth;
wherein the dispensation of the pre-culture medium is formulated as:
Half-Strength Basal Medium:
2.0-2.5 μM 6-benzylaminopurine;
4-8 g/L agar powder,
2.5-3.5% sucrose.

In the step S3 of the method of the present invention, the pH value of the medium is adjusted to 5.74 using acid. Preferably, the said acid reagent is hydrochloric acid. In the step S3 of the method of the present invention, the said sterilization is carried out under conditions of autoclaving at 121° C. and 0.1 MPa for 15-20 minutes.

In the step S5 of the method of the present invention, the said conditions for the light culture are: irradiation by GRO-LUX lamps; preferably, the irradiation intensity is 40 mmol·m$^{-2}$·s$^{-1}$.

For zygotic embryos with embryo maturity between 80-100%, it is generally unnecessary to rescue the seed embryos, and the seed embryos with the maturity of 80-100% can be directly put into the germination medium for germination culture. Provided is an in vitro culture and rescue technology for immature embryos of avocado in the present invention, in which the zygotic embryos at different development stages are induced to maturity under in vitro conditions, and the embryos are induced to germinate after maturity to form healthy plants. The technology of the present invention can increase the recovery rate of hybrid avocado seeds and reduce the waste of hybridization results.

DETAILED DESCRIPTION OF THE INVENTION

Figure 1:
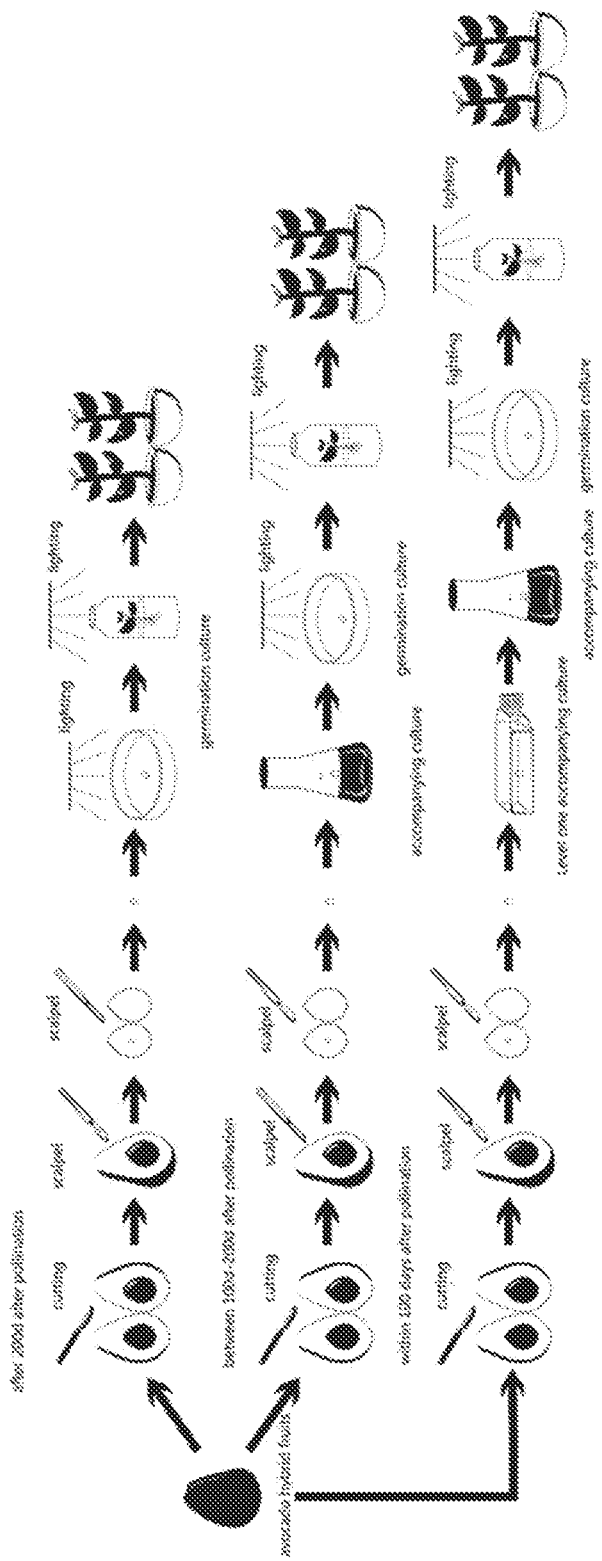
FIG. 1 is a schematic view of the flow of one embodiment of the method of the present invention.
Figure 2:
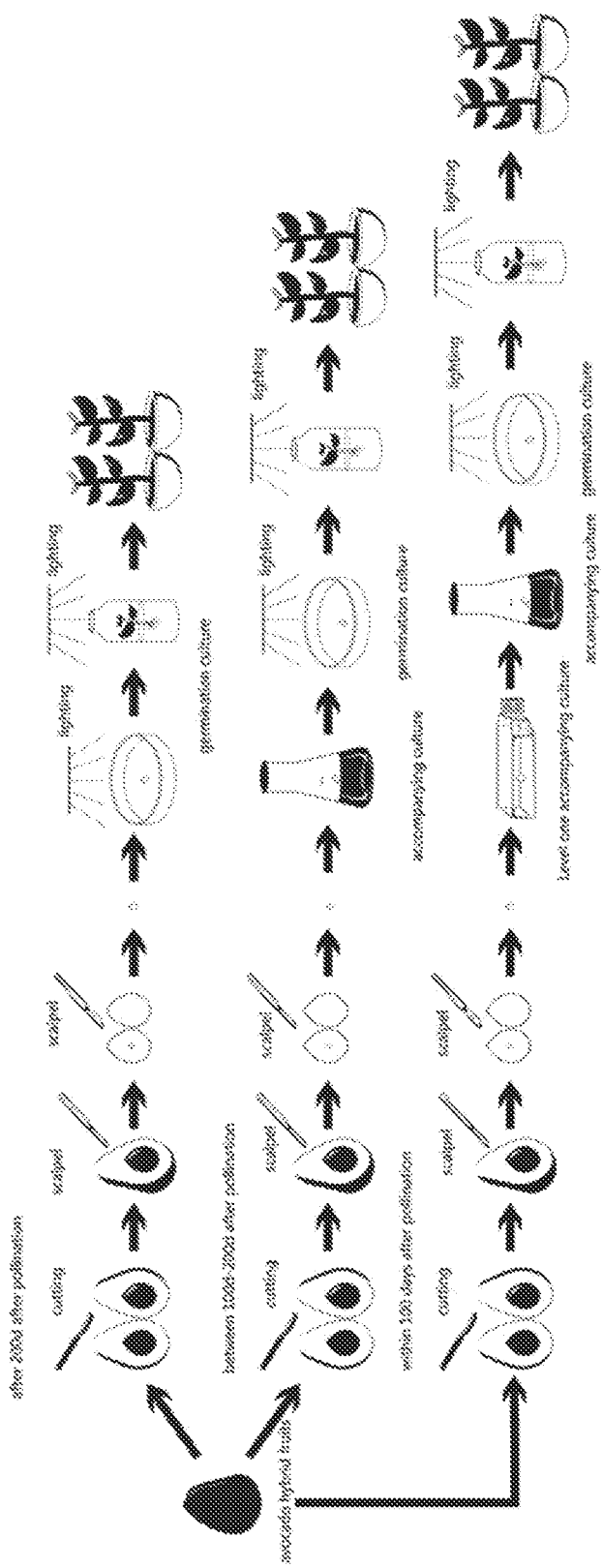
FIG. 2 is a schematic view of the process of another embodiment of the method of the present invention.

The present invention is further described below by specific embodiments.

Provided is a rescue method for immature embryo of avocado, and the said method comprising the steps as following:

step S1, pre-treatment of explants

For materials of physiological fruit drop, materials of other shedding and the materials that need embryo rescue, preferably performing the embryo rescue within 48 hours of fruit drop or fruitage falling, which helps increase the success rate of rescue.

After harvest, the fruits were sterilized on the surface by immersion in the 0.5% (v/v) sodium hypochlorite solution containing 10 drops/L of TWEEN 20 for 10 min, followed by rinsing in the sterile distilled water for three times. By sterilizing the fallen fruit and the seed embryos, to ensure a sterile state of the seed embryos, and ascertain the successful rescue of the seed embryos and correct results.

The sterilized fruits were cut longitudinally under aseptic conditions; the seeds were taken out and the fruits were sterilized on the surface by immersion in 0.5% (v/v) sodium hypochlorite solution for 10 minutes, followed by rinsing in sterile distilled water for three times. The. sterilized seeds were carefully stripped of the immature zygotic embryos.

step S2, Embryo basic maturation culture method

The maturity of the zygotic embryos is judged from practical experiences. Direct germination culture is performed on the zygotic embryos with 80%-100% embryo maturity. Put the zygotic embryos with 80%-100% embryo maturity into the germination medium for germination culture, and choose the intensity of germination medium according to the development status of avocado and embryo maturity; the medium intensity is chosen according to the different development status of avocado and embryo maturities; a liquid medium is chosen if the maturity is low, and a semi-solid medium is chosen if the maturity is moderate, meanwhile, according to the embryo development status, the culture medium is gradually changed from the liquid medium to the semi-solid culture medium and finally to solid culture medium.

Zygotic embryos with embryo maturity of 80% or less are the objects to be rescued.

Zygotic embryos with 80% or less embryo maturity were selected and cultured to 80-100% maturity, and the germination culture is performed next.

The media to be used for accompanying culture to germination culture include: (a) basal medium, (b) germination medium and (c) accompanying medium.

The dispensations of the three media listed above and the methods of preparation are described below.

The dispensation of the germination media is:

Basal Medium:

2.22 μM 6-BA;

6 g/L agar powder,

3% sucrose;

wherein the dispensation of the basal medium is shown in table 3 below:

TABLE 3

| | Ingredients of basal medium (mg/L) | concentration (mg/L) |
|---|---|---|
| Macroelements: | Potassium nitrate $KNO_3$ | 1900 |
| | Ammonium nitrate $NH_4NO_3$ | 1650 |
| | Potassium dihydrogen phosphate $KH_2PO_4$ | 170 |
| | Magnesium sulfate $MgSO_4 \cdot 7H_2O$ | 370 |
| | Calcium chloride $CaCl_2 \cdot 2H_2O$ | 440 |
| Trace elements: | Potassium iodide KI | 0.75 |
| | Boric acid $H_3BO_3$ | 3.0 |
| | Manganese sulfate $MnSO_4 \cdot H_2O$ | 10 |
| | Zinc sulfate $ZnSO_4 \cdot 7H_2O$ | 2.0 |
| | Sodium molybdate $Na_2MoO_4 \cdot 2H_2O$ | 0.25 |
| | Cobalt chloride $CoCl_2 \cdot 6H_2O$ | 0.025 |
| | Cupric sulfate $CuSO_4 \cdot 5H_2O$ | 0.025 |
| Iron salt: | Ethylenediaminetetraacetic acid disodium salt $Na_2 \cdot EDTA$ | 37.3 |
| | Ferrous sulfate $FeSO_4 \cdot 7H_2O$ | 27.8 |
| Organic composition: | Inositol | 100 |
| | Nicotinic acid VB5 | 1.0 |
| | Pyridoxine hydrochloride VB6 | 1.0 |
| | Thiamine hydrochloride VB1 | 10 |

Note: In the above table, iron salts were obtained in tissue culture by firstly dissolving disodium ethylenediaminetetraacetate (Na 2-EDTA) and ferrous sulfate $FeSO_4$-$7H_2O$ respectively, and then mixing with each other in the preparation.

① Choosing the accompanying medium according to different embryo maturations a total of 120 seed embryos within 100 days after pollination, 100 d-200 d after pollination and 200 d after pollination were selected from the fallen seeds of avocado, and the following media were respectively used for culture.

The dispensations of the accompanying media a, b, c, d, e, and f and the principles of selection are as follows.

For the seed embryos within 100 days after pollination, either of the accompanying media a or b is selected for the accompanying culture.

a. Half-strength basal medium
400 mg/L casein hydrolysate
10% coconut water
10% sucrose
2 g/L agar powder, b. Half-strength basal medium
400 mg/L glutamine
10% coconut water
10% sucrose
2 g/L agar powder For seed embryos at 100 to 200 days after pollination, either of the accompanying medium c or d is selected for accompanying culture.

c. Half-strength basal medium
400 mg/L casein hydrolysate
10% coconut water

5% sucrose
3 g/L agar powder;
d. Half-strength basal medium
400 mg/L glutamine
10% coconut water
5% sucrose
3 g/L agar powder.

For seed embryos after 200 days after pollination, either of the accompanying medium e or f is selected for accompanying culture.
e. Basal medium
400 mg/L casein hydrolysate
10% coconut water
3% sucrose
5 g/L agar powder,
f. Basal medium
400 mg/L glutamine
10% coconut water
3% sucrose
5 g/L agar powder.

The distributions of the dispensations for the 120 seed embryos and their accompanying media are shown in Table 4 below.

TABLE 4

| Embryo maturity | Number of embryos/granule | Dispensation of accompanying medium |
|---|---|---|
| within 100 days after pollination | 20 | a |
| | 20 | b |
| between 100 d-200 d after pollination | 20 | c |
| | 20 | c |
| after 200 d after pollination | 20 | e |
| | 20 | f | step S3, Preparation of culture solution

Adjusting the pH value of all the above accompanying media to 5.5-6.5 with hydrochloric acid, autoclaving the accompanying mediums at 121° C. and 0.1 MPa for 15-20 min; adding coconut water to the cooled and sterilized accompanying medium after cooling the accompanying media.

step S4, Selection and replacement of the accompanying media

In the pre-heart-shape stage of embryo culture, choosing media a or b, after the embryos were cultured into the torpedo stage, choosing medium c or d, and after maturity stage choosing medium e or f.

After 2-3 weeks of using the corresponding accompanying medium for each maturity, replacing the medium with a new one, or the accompanying medium being replaced to a accompanying medium for the next maturity according to the maturity of the seed embryos until the seed embryos mature.

The accompanying culture should be performed at 25° C. 1° C. with darkness or low light.

step S5, Germination culture

When the seed embryos in the accompanying culture reached the germination period, the seed embryos were placed in the germination medium for cultivation. Meanwhile, cotyledons on the accompanying medium were partially removed to induce the germination of the embryos, and the medium was replaced at an interval of 2-3 weeks.

In the germination culture, the seed embryos were kept growing at a temperature of 25° C. 1° C. Germination culture was carried out under light conditions with a 16 h photoperiodic incubation during the germination culture. The specific operations were: irradiation by GROLUX lamp with an irradiation intensity of 40 $mmol·m^{-2}·s^{-1}$; the irradiation intensity is 1 KLux=18 $\mu mol·m^{-2}·s^{-1}$ under solar light source during the daytime, to promote the growth of the plants until they were cultured into normal rooted seedlings.

TABLE 5

Summary of seed embryo rescue results of avocado

| Embryo maturity | Number of embryos/granule | Dispensation of accompanying medium | rescue results |
|---|---|---|---|
| within 100 days after pollination | 20 | a | 75% |
| | 20 | b | 76% |
| between 100 d-200 d after pollination | 20 | c | 90% |
| | 20 | c | 90% |
| after 200 d after pollination | 20 | e | 95% |
| | 20 | f | 96% |

As is seen from Table 5, the success rate of rescue of the seed embryos with lower maturity (e.g., within 100 days after pollination) is lower than that of the seed embryos with higher maturity. For the seed embryos pollinated for more than 200 days with higher maturity, the success rate of rescue could exceed 95%, and the rescue and recovery of most seed embryos are achieved.

Through the method of the present invention, the fruit fallen in the process of hybridization culture of avocado can be rescued, and the recovery and effective use of the fallen seeds of avocado are realized, and the loss of hybridization results are reduced. The technology of the present invention can effectively improve the survival rate of zygotic embryos of hybrid avocado, increase the success rate of avocado hybridization, rescue the hybrid offspring, reduce the loss of hybrid offspring, ensure the genetic integrity of the hybrid group, and provide key technology for avocado hybrid breeding and genetic research, etc.

The invention claimed is:

1. An in vitro rescue method for immature embryo of avocado, characterized in that the said method comprises:
   (a) pre-treatment of explants comprising: collecting immature fallen fruits of avocado, performing embryo rescue within 48 hours of fruit drop collected, stripping immature zygotic embryos from fallen sterilized fruits, selecting zygotic embryos with maturity below 80%, increasing the maturity, to 80-100% by accompanying culture, and performing a germination culture;
   (b) preparing a basal medium, accompanying media and a germination medium according to dispensations, wherein the dispensation of the basal medium is shown below:

|  | Ingredients of basal medium (mg/L) | concentrations (mg/L) |
|---|---|---|
| Macroelements: | Potassium nitrate KNO$_3$ | 1900 |
|  | Ammonium nitrate NH4NO$_3$ | 1650 |
|  | Potassium dihydrogen phosphate KH$_2$PO$_4$ | 170 |
|  | Magnesium sulfate MgSO$_4$•7H$_2$O | 370 |
|  | Calcium chloride CaCl$_2$•2H$_2$O | 440 |
| Trace elements: | Potassium iodide KI | 0.75 |
|  | Boric acid H$_3$BO$_3$ | 3.0 |
|  | Manganese sulfate MnSO$_4$•4H$_2$O | 10 |
|  | Zinc sulfate ZnSO$_4$•7H$_2$O | 2.0 |
|  | Sodium molybdate Na$_2$MoO$_4$•2H$_2$O | 0.25 |
|  | Cobalt chloride CoCl$_2$•6H$_2$O | 0.025 |
|  | Cupric sulfate CuSO$_4$•5H$_2$O | 0.025 |
| Iron salt: | Ethylenediaminetetraacetic acid disodium salt Na$_2$•EDTA | 37.3 |
|  | Ferrous sulfate FeSO$_4$•7H$_2$O | 27.8 |
| Organic composition: | Inositol | 100 |
|  | Nicotinic acid VB5 | 1.0 |
|  | Pyridoxine hydrochloride VB6 | 1.0 |
|  | Thiamine hydrochloride VB1 | 10 | the dispensations of accompanying medium a, medium b, medium c, medium d, medium e and medium f are as follows:
medium a: half-strength basal medium
  300 to 500 mg/L casein hydrolysate
  8-12% coconut water
  8-12% sucrose
  1-3 g/L, agar powder,
medium b: half-strength basal medium
  400 mg/L glutamine
  8-12% coconut water
  8-12% sucrose
  1-3 g/L agar powder,
medium c: half-strength basal medium
  300-500 mg/L casein hydrolysate
  8-12% coconut water
  4-6% sucrose
  2-4 g/L agar powder,
medium d: half-strength basal medium
  300-500 mg/L glutamine
  8-12% coconut water
  4-6% sucrose
  2-4 g/L, agar powder,
medium e: basal medium
  300-500 mg/L casein hydrolysate
  8-12% coconut water
  2-4% sucrose
  4-6 g/L agar powder, and
medium f: basal medium
  300-500 mg/L glutamine
  8-12% coconut water
  4-6% sucrose
  4-6 g/L agar powder;
the dispensation of the germination medium is shown below:
  basal medium
  2.22 µM 6-benzylaminopurine
  6 g/L agar powder
  2.5-3.5% sucrose;
wherein the preparing comprises adding, for each medium, each component other than coconut water into a vessel respectively, adding the coconut water into the vessel, stirring, adjusting a pH value of each medium to 5.5-6.5, sterilizing and cooling the media, to thereby obtain the basal medium, the accompanying medium a, medium b, medium c, medium d, medium e, and medium f, and the germination medium;

(c) selection of initial accompanying media selecting the appropriate dispensations of the accompanying media according to different maturities of zygotic embryos, selecting the zygotic embryos within 100 days after pollination with either of accompanying medium a or medium b as the initial accompanying medium, selecting the zygotic embryos between 100 and 200 days after pollination with either of accompanying medium c or medium d as the initial accompanying medium, and selecting the zygotic embryos after 200 days after pollination with either of accompanying medium e or medium f as the initial accompanying medium;

(d) performing the accompanying culture of zygotic embryos comprising:
during pre-heart-shape stage of the zygotic embryos, using the medium a or medium b for the accompanying culture, and when the zygotic embryos are cultured into torpedo stage, replacing the accompanying medium a or medium b by the accompanying medium c or medium d, respectively, when the zygotic embryos are cultured into the maturation stage, replacing the accompanying medium by the accompany medium e or medium f, respectively, and wherein the accompanying culture is carried out under dark conditions;

(e) germination culture comprising:
culturing the zygotic embryos obtained from the accompanying culture in the germination medium at 25° C.±1° C. under light conditions until the zygotic embryos are cultured into rooted seedlings.

2. The method according to the claim 1, characterized in step (a), the surface of the immature fallen fruits and the zygotic embryos are sterilized.

3. The method according to the claim 2, characterized in that sterilization treatment comprises: soaking in a 0.5 v/v % sodium hypochlorite solution followed by rinsing in sterile distilled water for three times.

4. The method according to claim 1, characterized in the step S2, the dispensations of the accompanying medium a, medium b, medium c, medium d, medium e, medium f are as follows;
medium a: half-strength basal medium
  400 mg/L casein hydrolysate
  10% coconut water 10% sucrose
2 g/L agar powder,
medium b: half-strength basal medium
    400 mg/L glutamine
    10% coconut water
    10% sucrose
    2 g/L agar powder,
medium c: half-strength basal medium
    400 mg/L casein hydrolysate
    10% coconut water
    5% sucrose
    3 g/L agar powder,
medium d: half-strength basal medium
    400 mg/L glutamine
    10% coconut water
    5% sucrose
    3 g/L agar powder,
medium e: basal medium
    400 mg/L casein hydrolysate
    10% coconut water
    3% sucrose
    5 g/L agar powder, and
medium f: basal medium
    400 mg/L glutamine
    10% coconut water
    3% sucrose
    5 g/L agar powder.

5. The method according to claim 1, characterized in the step (c), for the zygotic embryos within 100 days after pollination, if the initial accompanying culture is selected for poor results or for poor development, after stripping the zygotic embryos of their seed coats and sterilizing them, the zygotic embryos are maintained at a temperature of 25° C.±1° C. in a pre-culture medium with 16 hours of light irradiation during maintenance growth, and continuing the rescue of immature zygotic embryos after the seeds return to normal growth, wherein the dispensation of the pre-culture medium is formulated as follows:

half-strength basal medium
        2.0-2.5 μM 6-benzylaminopurine;
        4-8 g/L agar powder; and
        2.5-3.5% sucrose.

6. The method according to claim 1, characterized in the step (c), the pH value of the medium is adjusted to 5.74 using a hydrochloric acid reagent.

7. The method according to claim 1, characterized in the step (c), sterilization condition is autoclaving at 121° C. and 0.1 MPa for 15-20 minutes.

8. The method according to claim 1, characterized in the step (e), the conditions of said light culture are: irradiation by lamps to ensure plant growth and an irradiation intensity is 40 mmol·m$^{-2}$·s$^{-1}$.

\* \* \* \* \*